United States Patent [19]

Pernetti et al.

[11] Patent Number: 5,762,382
[45] Date of Patent: Jun. 9, 1998

[54] INTERLOCKING DUAL SEAL CUFF/PORT INTERFACE

[75] Inventors: Denise L. Pernetti, Cottage Grove; Richard T. Hutter, Prairie Du Sac, both of Wis.

[73] Assignee: Ohmeda Inc., Liberty Corner, N.J.

[21] Appl. No.: 695,686

[22] Filed: Jul. 12, 1996

[51] Int. Cl.$^6$ ............................................. F16L 47/06
[52] U.S. Cl. ........................... 285/351; 285/921; 285/239
[58] Field of Search ................................. 285/351, 921, 285/319, 238, 239

[56] References Cited

U.S. PATENT DOCUMENTS

| | | | |
|---|---|---|---|
| 4,030,850 | 6/1977 | Hyde | 285/921 |
| 4,779,920 | 10/1988 | Lee | 285/921 |
| 5,078,430 | 1/1992 | St. Onge | 285/921 |
| 5,180,197 | 1/1993 | Thompson, Jr. | 285/921 |
| 5,360,242 | 11/1994 | Argent | 285/921 |

FOREIGN PATENT DOCUMENTS

| | | | |
|---|---|---|---|
| 2812884 | 9/1978 | Germany | 285/921 |
| 3956 | 5/1989 | WIPO | 285/921 |

*Primary Examiner*—Eric K. Nicholson
*Attorney, Agent, or Firm*—Roger M. Rathbun; Salvatore P. Pace

[57] ABSTRACT

A connection, preferably for use in a medical environment, for joining a rigid circular port from a medical machine to an elastomeric hose cuff having a medical hose extending therefrom. The rigid cuff has an external annular bead formed at its outward end while the elastomeric hose cuff has an internal annular bead formed at its distal end. When the components are coupled together by sliding the hose cuff over the rigid port, a double seal is formed between the various annular beads and the surfaces of the component to provide a substantially leakproof seal between the elastomeric hose cuff and the rigid port to prevent gasses from escaping to the surrounding environment.

7 Claims, 3 Drawing Sheets

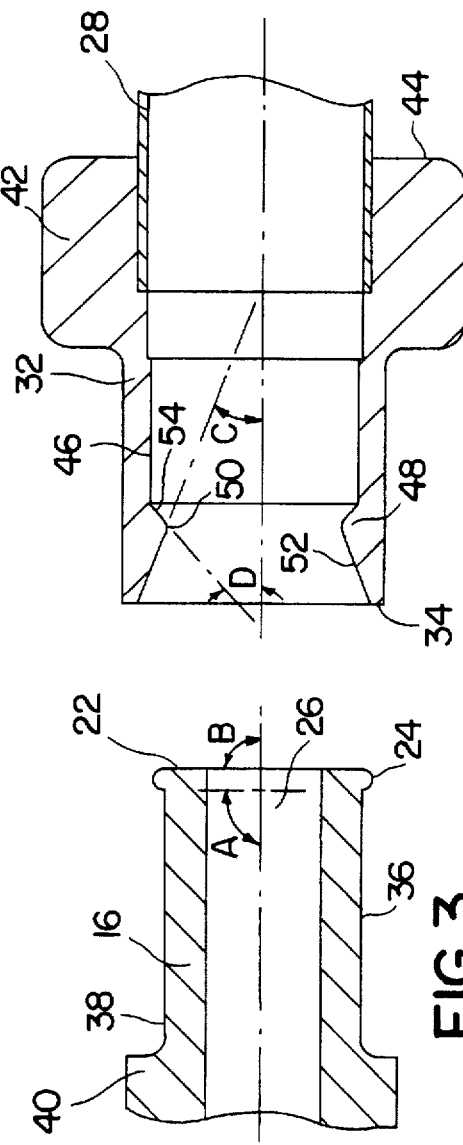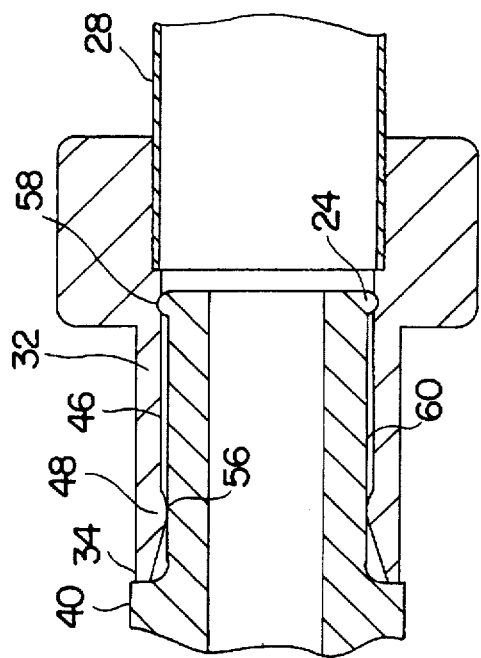

INTERLOCKING DUAL SEAL CUFF/PORT INTERFACE

BACKGROUND OF THE INVENTION

The present invention relates to a connection between a flexible hose and a rigid port and, more particularly, to an improved connection comprising a specially molded hose cuff that is connected to a rigid port and particularly suited for use in a medical environment.

There are numerous applications, particularly in the atmosphere of an operating room or other hospital locations, that flexible medical hoses are connected to various machines, such as anesthesia machines, ventilators and the like and a fluid, generally gas, is transmitted within the hoses. Such hoses are typically connected to various size ports on such machines.

It is of utmost importance that the connections be leak proof inasmuch as the fluids contained and transmitted in the hoses are generally of the type that should not enter the ambient atmosphere. As an example, the hoses may carry a volatile anesthetic that is being administered to a patient for anesthesia and the release of such anesthetic agent into the surrounding atmosphere can be deleterious to the performance of the personnel and constitute a health hazard. In addition, the hoses may well carry gasses exhaled by the patient and, again, pose a health risk if released to enter the outer environment and breathed by the surrounding personnel.

Accordingly, it is also important that such medical hoses be readily and conveniently attached and detached from such machines since there is a need to easily make such connections in setting up the equipment. It is also convenient that disconnection of the medical hoses from such machines be readily accomplished, however, the disconnection preferably is more difficult than connecting since it is advantageous to prevent inadvertent or accidental disconnects. At the same time, it is important that the connections, when made, be leakproof so as to completely contain the fluid within the hoses.

SUMMARY OF THE INVENTION

The interlocking dual seal cuff/port interface of the present invention overcomes the foregoing difficulties by providing a flexible elastomeric hose cuff at the end of a medical hose that fits over a rigid port and interconnects therewith to form a double seal that discourages leaks to the atmosphere. The elastomeric hose cuff and the rigid port are readily attached to each other yet the disconnection of the medical hose from the rigid port is more difficult in order to reduce the risk of an inadvertent disconnection.

In the present invention, the rigid port, generally from an anesthesia machine, ventilator or the like has a known external diameter and has an external annular bead at its outer, distal end. The elastomeric hose cuff has a known internal diameter and has an internal annular bead located at its distal end. In assembling or connecting the hose cuff to the rigid port, the hose cuff slides over the rigid port. In making that connection, therefore, the internal annular bead of the elastomeric hose cuff seals against the external diameter of the rigid port at the same time that the internal diameter of the elastomeric hose cuff seals against the external annular bead of the rigid port. Thus, the overall connection is provided with dual seals that are spaced a finite distance apart such that gasses are prevented from escaping the connection.

In addition, there is a gradual internal slope leading from the distal end of the elastomeric hose cuff to the internal bead of the elastomeric hose cuff such that it can be easily slid over the annular bead of the port as the hose is attached to the port. On the other hand, however, there is a relatively sharp transition on the opposite side of the internal bead such that the external bead of the port cannot easily pass in the direction to detach the hose cuff from the port, thereby making removal of the elastomeric hose cuff difficult from the rigid port.

BRIEF DESCRIPTION OF THE DRAWINGS

FIG. 3 is a cross sectional view of a typical rigid port used with the present invention;

FIG. 4 is a cross sectional view of a flexible elastomeric hose cuff used with the present invention; and FIG. 5 is a cross-sectional view of a completed connection between the rigid cuff of FIG. 3 and the flexible hose cuff of FIG. 4.

DESCRIPTION OF THE PREFERRED EMBODIMENT

Figure 1:
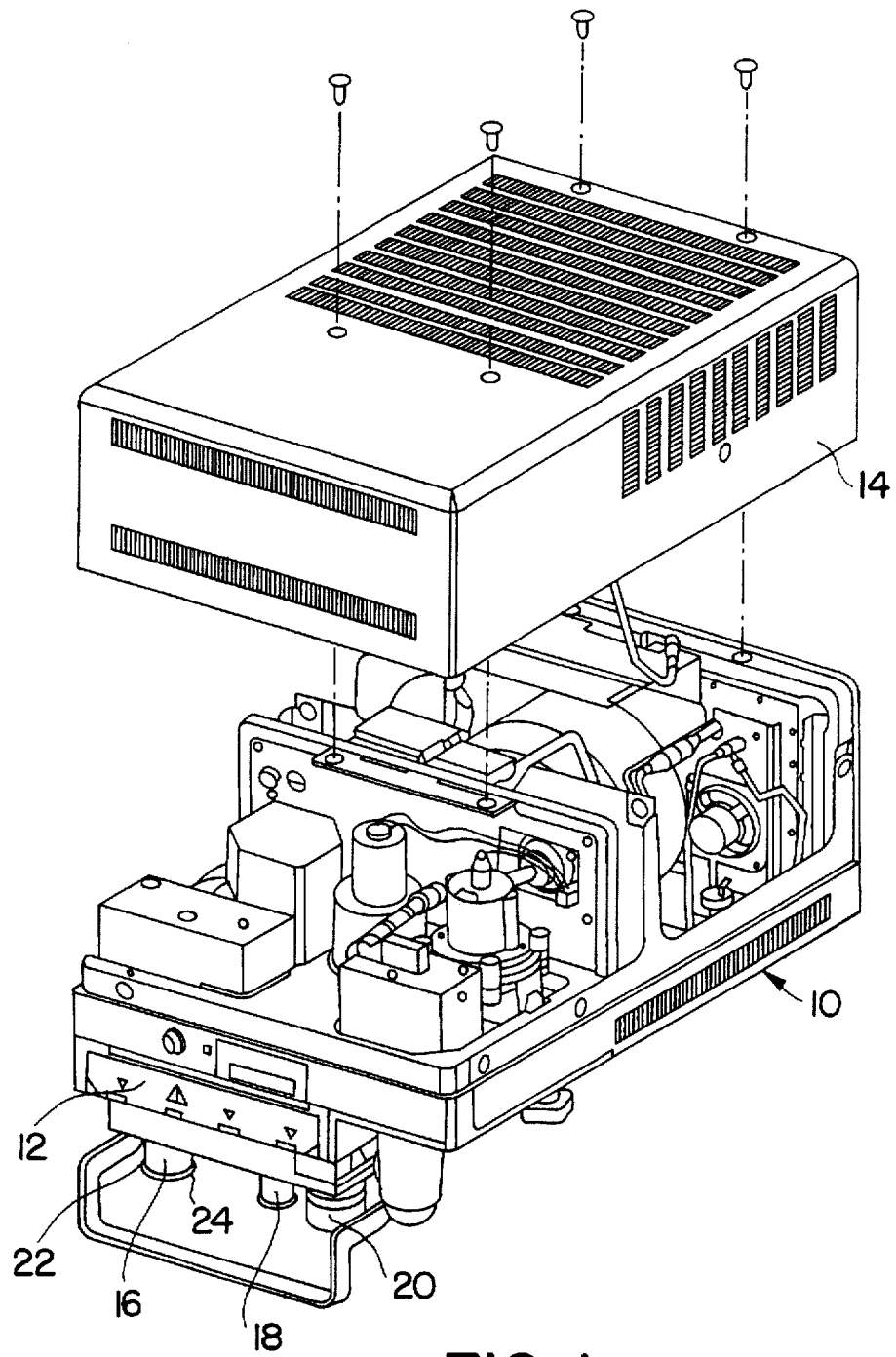
FIG. 1 is an isometric view of an anesthesia ventilator having a manifold with ports that are usable with the present invention.

Referring now to FIG. 1, there is shown an isometric view of an anesthesia ventilator 10 having a fluid manifold 12 attached thereto. The anesthesia ventilator 10 is a commercial machine for ventilating a patient and is typical of the type of medical equipment for which the present invention is adapted.

The anesthesia ventilator 10 is shown with the cover 14 removed and the internal components visible. The fluid manifold 12 is adapted to be readily removed from the anesthesia ventilator 10 for cleaning and a number of rigid ports 16, 18 and 20 extend from the fluid manifold 12 for connection to medical hoses to carry gasses to and/or from the anesthesia ventilator 10 in carrying out its function in ventilating a patient.

Figure 2:
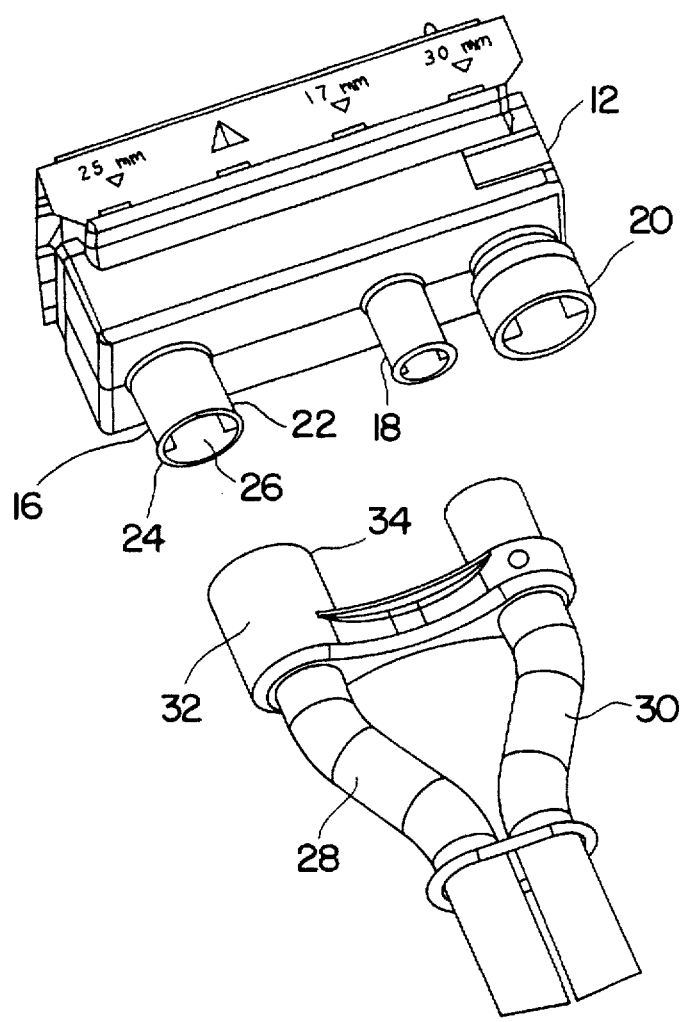
FIG. 2 is an isometric view of the manifold of the anesthesia ventilator of FIG. 1, and showing a medical hose in position to be connected to a rigid port of such manifold.

Turning now to FIG. 2, there is shown an isometric view of the fluid manifold 12 and having the ports 16, 18 and 20 extending outwardly therefrom. As will be used in the present description, the end of each of the ports extending from the fluid manifold will be referred to as the distal end of that rigid port. Since the rigid ports 16, 18 are, for purposes of explaining the present invention, the same in construction, the description will refer specifically to the rigid port 16 and its distal end 22. As can be seen, the rigid port 16 extends outwardly in a uniform external diameter and has an annular external raised bead 24 at the distal end 22. The rigid port 16 further has an internal opening 26 for the passage of fluid into or out of the fluid manifold 12.

Also shown in FIG. 2 is a pair of medical hoses 28 and 30 that connect to the rigid ports 16 and 18 to provide for the passage of fluids between the fluid manifold 12 and the medical hoses 28 and 30. When referring to the medical hoses 28 and 30, the end that is attached to the rigid ports 16 and 18 will be referred to for convenience as the distal end. Therefore, taking the medical hose 28, a elastomeric flexible hose cuff 32 is affixed to the distal end of the medical hose 28 and, carrying forward the same convention, the flexible hose cuff 32 has its distal end 34 that initially fits over the rigid port 16 in making the connection between the two components.

Turning now to FIG. 3, there is shown a cross-sectional view of the rigid port 16 with a cylindrical body 36 of a known external diameter and its distal end 22 having formed thereon, an annular external raised bead 24, again, of predetermined or known external diameter. At the proximal end 38 of the rigid port 16, there is formed a hub 40 which is a transitional area to the overall fluid manifold 12. As may be seen in FIG. 3, the annular external raised bead 24 is preferably in the shape of a semicircular side cross-section, that is, the edges of the raised bead form angles of 90 degrees with respect to the longitudinal centerline of the rigid port 16 as shown by the angles A and B. As it also may been obvious, the angle B may be a gradual sloped angle, such as at about 15 to about 25 degrees in order to ease the coupling of the flexible hose cuff 32 to the rigid port 16 as will become apparent.

Turning now to FIG. 4, there is shown a cross-sectional view of the elastomeric hose cuff 32 used with the present invention. A thick portion 42 is molded at the proximal end 44 of the elastomeric hose cuff 32 and provides for ease of handling by the user in connecting and disconnecting the elastomeric hose cuff 32 to the rigid port 16. The medical hose 28 has its distal end fitted within and sealed to the interior of the proximal end 44 of the elastomeric hose cuff 32 in conventional construction.

As also can be noted, the elastomeric hose cuff 32 has a uniform internal diameter, shown at 46 and also has an annular internal raised bead 48 located at or adjacent the distal end 34 of the elastomeric hose cuff 32. The internal diameter of annular internal raised bead 48 at its apex 50 is predetermined or a known dimension. Between the apex 50 of the annular internal raised bead 48 is a transition sloping surface 52 leading to the distal end 34 of the elastomeric hose cuff 32. Preferably the transition sloping surface 52 is formed at an angle of between about 15 to about 25 degrees with respect to the longitudinal axis of the elastomeric hose cuff 32, shown in FIG. 4 as angle C. The preferred angle is about 21 degrees.

A sharp transition surface 54 is formed from the apex 50 of the annular internal raised bead 48 toward the proximal end 44 of the elastomeric hose cuff 32, the purpose of which will be explained. Preferable the angle of that sharp transition surface 54 is between about 40 degrees to about 90 degrees with respect to the longitudinal centerline of the elastomeric hose cuff 32. The preferred angle is about 45 degrees an is indicated as the angle D in FIG. 4.

Turning, finally, to FIG. 5, there is shown a cross-sectional view of an elastomeric hose cuff 32 in position connected to rigid port 16. As can be seen, the actual connection of the components is by sliding the elastomeric hose cuff 32 onto rigid port 16 and, as that connecting process begins, the annular external bead 24 of the rigid port 16 encounters the transition sloping surface 54 of the elastomeric hose cuff 32 such that it is easy to slide the elastomeric hose cuff 32 over that annular external bead 32 due to the angle of the transition sloping surface 52 and the flexibility of the elastomeric hose cuff itself.

Thus, the connecting of he components is easily accomplished and the elastomeric hose cuff 32 is continued to be slid over the rigid port 16 until the distal end 34 of the elastomeric hose cuff 32 abuts against the hub 40. At this point, the connection is fully accomplished and a seal formed between the annular internal raised bead 48 of the elastomeric hose cuff 32 and the external diameter surface of the rigid port 16 and shown on FIG. 5 at 56. The seal is a circular seal surrounding the periphery of the rigid port 16.

A second seal is formed at 58 between the internal diameter surface 46 of the elastomeric hose cuff 32 and the annular external bead 24 of the rigid port 16.

Thus, two circular seals are formed between the elastomeric hose cuff 32 and the rigid port 16 thereby preventing the leakage of fluid from the internal passages of the connecting components. A dead volume 60 separates the two seals and provides a finite distance between the seal at 56 and the seal at 58.

In disconnecting the elastomeric hose cuff 32 from the rigid port 16, it can be seen that the sharp transition surface 54 first encounters the annular external raised bead 24 to accomplish the removal of the elastomeric hose cuff 32. Since the angle of the sharp transition surface 54 is a steep angle, as described, considerable more force must be exerted in removing the elastomeric hose cuff 32 than in connecting the elastomeric hose cuff 32 to the rigid port 16. Thus the disconnection must be fairly deliberate, with considerable force, and the potential of inadvertent or accidental disconnection is reduced.

While the present embodiment has been set forth in terms of a specific embodiment, it will be understood that the hose/port interface herein disclosed may be modified or altered by those skilled in the art to other configurations. Accordingly, the invention is to be broadly construed and limited only by the scope and spirit of the claims appended hereto.

We claim:

1. An elastomeric hose cuff for connecting a hose to a rigid circular port having a predetermined external diameter and an annular external raised bead formed at the distal end thereof, said elastomeric hose cuff having a distal end adapted to be fitted over the rigid port to connect said elastomeric hose cuff to the rigid port and a proximal end having a length of hose extending therefrom, said elastomeric hose cuff having a predetermined internal diameter adapted to fit over and form a first seal when fitted over the annular external raised bead of the port and having an annular internal raised bead located at said distal end having a predetermined internal diameter to form a second seal between said internal annular internal raised bead and the predetermined external diameter of the port when said elastomeric hose cuff is fitted over the port to form a double fluid sealed connection between the rigid circular port and said elastomeric cuff, said annular internal raised bead having a gradual sloping internal transition surface from said annular internal raised bead toward said distal end of said elastomeric hose cuff and a sharp internal transition surface from said annular internal raised bead transition and said internal diameter of said cuff toward said proximal end whereby said elastomeric cuff is readily attachable and removable from a rigid circular port.

2. An elastomeric hose cuff as defined in claim 1 wherein said gradual sloping internal transition surface is at an angle of from about 15 to about 25 degrees with respect to the longitudinal centerline of said elastomeric hose cuff.

3. An elastomeric hose cuff as defined in claim 2 wherein said angle is about 21 degrees.

4. An elastomeric hose cuff as defined in claim 1 wherein said sharp transition surface is formed at an angle of between about 40 degrees and 90 degrees with respect to the longitudinal centerline of said elastomeric hose cuff.

5. An elastomeric hose cuff as defined in claim 4 wherein said sharp transition surface is formed at an angle of about 45 degrees.

6. A connection between a rigid port and an elastomeric hose cuff having a predetermined internal diameter, said port having a distal end adapted to receive said elastomeric hose, said port having a having a predetermined diameter and having a raised external annular bead that creates a first gas tight seal between said external annular bead and the predetermined internal diameter of said hose cuff, said hose cuff having a distal end adapted to fit over said rigid port and having an internal annular raised bead of predetermined internal diameter to form a second gas tight seal with the predetermined external diameter of said rigid cuff, said internal annular raised bead having a gradual sloping internal transition surface from said annular internal raised bead toward said distal end of said elastomeric hose cuff and having a sharp transition surface between said annular internal raised bead and said internal diameter of said cuff toward said proximal end, said first and second seals being separated by a finite distance to form a double seal between said rigid port and said elastomeric hose cuff.

7. A connection as defined in claim 6 wherein said first and second seals form a dead space between said rigid port and said elastomeric hose cuff.

* * * * *